(12) United States Patent
Gillette et al.

(10) Patent No.: US 7,425,301 B2
(45) Date of Patent: Sep. 16, 2008

(54) METHOD FOR PROVIDING OZONE SANITATION OF FRUITS AND VEGETABLES

(75) Inventors: Thomas D. Gillette, Burley, ID (US); James M. Gillette, Burley, ID (US)

(73) Assignee: Fresh Food Technology, Inc., Burley, ID (US)

( * ) Notice: Subject to any disclaimer, the term of this patent is extended or adjusted under 35 U.S.C. 154(b) by 128 days.

(21) Appl. No.: 10/306,168

(22) Filed: Nov. 26, 2002

(65) Prior Publication Data

US 2003/0156978 A1 Aug. 21, 2003

Related U.S. Application Data

(60) Provisional application No. 60/333,428, filed on Nov. 26, 2001.

(51) Int. Cl.
*A61L 2/18* (2006.01)
(52) U.S. Cl. .......................... 422/28; 426/506; 426/509
(58) Field of Classification Search ............... 422/28, 422/186.07; 210/760; 426/506, 508, 509
See application file for complete search history.

(56) References Cited

U.S. PATENT DOCUMENTS

| | | | | |
|---|---|---|---|---|
| 5,227,184 | A | 7/1993 | Hurst | 426/312 |
| 5,403,602 | A | 4/1995 | Endico | 426/231 |
| 5,560,831 | A | 10/1996 | Bladen et al. | 210/704 |
| 5,720,905 | A | 2/1998 | Ho | 261/16 |
| 5,824,274 | A | 10/1998 | Long | 422/186.07 |
| 5,858,430 | A * | 1/1999 | Endico | 426/241 |
| 5,891,499 | A | 4/1999 | Balsano | 426/335 |
| 5,927,304 | A | 7/1999 | Wen | 134/153 |

(Continued)

FOREIGN PATENT DOCUMENTS

JP 08103176 A * 4/1996

OTHER PUBLICATIONS

Advertisement: "Ozone Sanitation ARS 2000," Fresh Food Equipment LLC, 1051 Hansen Ave., Burley, ID 83318, 1 page.

(Continued)

*Primary Examiner*—Jill Warden
*Assistant Examiner*—Sean E. Conley
(74) *Attorney, Agent, or Firm*—Kirton & McConkie; David T. Tingey (57) ABSTRACT

The present invention features an ozone sanitation device and system and a method of using the same to sanitize various objects in various environments. The present invention is particularly adapted to be used to sanitize food products, such as fruit and vegetable products as well as others at the site of the marketing and selling of such products. The ozone sanitation device functions to combat harmful pathogens by reduce microbial growth and bacteria existing on the treated object. The device comprises an ozone generator that produces ozone gas that mixes with temperature controlled water to create an ozonated water solution to be applied to an object for treatment. Moreover, the present invention features several methods of using the ozone sanitation device to treat various objects, as well as a method for restoring water to dehydrated objects, such as fruits and vegetables. The method provides a continuous process and comprises using a tepid wash solution cycle and a chilled wash solution cycle of water and the application of ozone and oxygen.

19 Claims, 5 Drawing Sheets

U.S. PATENT DOCUMENTS

| | | | |
|---|---|---|---|
| 5,951,921 A * | 9/1999 | Koganezawa et al. | 261/36.1 |
| 6,120,822 A | 9/2000 | Denvir et al. | 426/320 |
| 6,132,629 A * | 10/2000 | Boley | 210/760 |
| 6,287,515 B1 * | 9/2001 | Koosman et al. | 422/22 |
| 6,379,633 B1 * | 4/2002 | Garlick | 422/305 |
| 6,506,309 B1 * | 1/2003 | Daniels et al. | 210/760 |
| 2004/0022908 A1 * | 2/2004 | Kanaya et al. | 426/506 |

OTHER PUBLICATIONS

Advertisement: "SPS 4000," Fresh Food Equipment LLC, 1051 Hansen Ave., Burley, ID 83318, 1 page.

Advertisement: "Ozone Sanitation Ozotech5000," Fresh Food Technology, Inc., P.O. Box 808, Burley, ID 83318, 1 page.

Advertisement: "Ozofresh 1 1000," Fresh Food Technology, Inc., P.O. Box 808, Burley, ID 83318, 1 page.

Advertisement: "Ozofresh R 1000," Fresh Food Technology, Inc., P.O. Box 808, Burley, ID 83318, 1 page.

Advertisement: "Ozofresh R 5000," Fresh Food Technology, Inc., P.O. Box 808, Burley, ID 83318, 1 page.

* cited by examiner

METHOD FOR PROVIDING OZONE SANITATION OF FRUITS AND VEGETABLES

RELATED APPLICATIONS

This application claims priority to U.S. Provisional Application Ser. No. 60/333,428, filed Nov. 26, 2001, and entitled, "Ozone Sanitation Unit," which is hereby incorporated by reference in its entirety.

BACKGROUND

1. Field of the Invention

The present invention relates to sanitizing devices and systems, and in particular to an ozone sanitation device and system for washing, sanitizing, and re-hydrating various objects. The present invention is particularly adapted for use in the food products industry, wherein various food products, such as fruits and vegetables, may be sanitized using a more natural ozone solution.

2. Background of the Invention and Related Art

The existence of harmful pathogens on various products poses a serious health risk to consumers, particularly when these products are consumed or otherwise introduced into the body. For example, there is an acute awareness in the food products industry of the existence of bacteria, viruses, and other harmful pathogens that grow and seemingly thrive on the food products being sold. Likewise, the medical field is also greatly concerned that the tools and products they use are free from such pathogens.

With an emphasis on food products, the supermarket industry is concerned that food products contain large counts of pathogens. They want to decrease their liabilities to any or all consumer food borne illnesses and deaths by decreasing the pathogens on the products sold. However, they also want to try and maximize revenue.

Along with the selling of bulk produce, it has become popular in the supermarket industry to sell cut and prepared produce. Both cut and uncut products carry pathogens and need to be sanitized. Although both are potentially dangerous, the prepared produce has a greater need for bacteria reduction because it has been cut and more surface area of the produce is exposed to probable contamination.

The chilled food industry has seen many changes the past number of years. There are many more packaged chilled products available from salads to fresh salsas, fresh cut vegetables to fresh cut fruits, with fruit being offered only in limited supply due to the shortened shelf-life and microbial bacterial problems. As the industry moves to more source processing, the food contamination risks have increased. There are also temperature abuse problems that develop. Temperature abuse problems come as a result of improper cooling in a refrigerated truck trailer, product left out of refrigeration on either the shipping or receiving ends. Improper handling at the source supplier is also a factor.

Because of the varied problems, many retail grocers and restaurant chains have gone back and forth in sourcing ready to use packaged chilled products. When chilled packaged lettuce products were first introduced, it was assumed and believed that they could ship from processing plants located at the source to all market areas. This proved to be a false assumption and the processors were forced to build processing plants strategically located throughout the country. Many advances have been made in packaging and processing technologies. However, there remains a large number of products, mainly fresh cut fruits, that are still to difficult to manufacture at a source processing plant and distribute to a wide area.

Moreover, as there are significant microbial and bacteria problems in whole fruits and vegetables, many of the retail grocers and restaurant chains have mandated inspections and certifications of whole fruits and vegetables shipped to them from the source supplier. The Center for Disease Control estimates some 75 million food borne illnesses and over 5,000 deaths each year are attributed to food borne pathogens, of which fully 50 percent are related to fruit and produce items. Changing lifestyles and imported chilled food products have contributed to the rapid emergence of new food borne pathogens.

Prior art devices and systems designed to combat or reduce many of the above-described problems tend to be inefficient, ineffective, or too expensive, thus rendering them largely inadequate, impractical, and/or inept and severely deficient. Many prior art concepts utilize traditional methods of dealing with bacteria, viruses, and spoilage of food products. These traditional methods consist of some variant of hiring a team of individuals to scrub food by hand with a diluted chlorine wash or another anti-bacterial and anti-viral agent, remove and discard the spoiled sections of a particular food product, and continue to monitor the food product's rapid spoilage. Additionally, there was little that could be done about the dehydration and shrinkage that occurs when a food product suffers a depletion in its moisture content.

Some of the modern systems of dealing with bacteria and viruses on food products are effective, but are unattractive to end use consumers and do little or nothing to slow spoilage, and even destroy some of the nutritional value of the food product upon treatment. Specifically, irradiation of food products, often referred to as cold pasteurization, has proven adequate to sterilize, but does nothing to enhance or even preserve the food product's good looks, water weight, and flavor. Also, many other problems exist with irradiation, such as expense.

Accordingly, what is needed is a device and system that adequately combats the overgrowth of bacteria, viruses, and other harmful pathogens, as well as prevents spoilage, without sacrificing or resultantly reducing those things that are desired and beneficial in the food product. What is also needed is a simple method of treating food products and associated objects to obtain these advantages.

SUMMARY AND OBJECTS OF THE INVENTION

As described above, the specter of harmful pathogens, namely bacteria and viruses, existing and overgrowing on or within food products presents a significant problem to both consumers of these products, as well as those in the business of producing, processing, transporting, supplying, and providing such products. Indeed, the problem is of such great significance and concern that several prior art devices, systems, treatments, etc., many of which are described above, have been developed and are in use for the purpose of preventing the disastrous effects that may be caused by these harmful pathogens. However, as noted above, the deficiencies in the prior art are significant, with marginally effective results, frequent undesired effects, and much inefficiency, thus leading to the provision of only limited solutions to the problems currently existing.

In light of these deficiencies, it is an object of some embodiments of the present invention to provide a new, unique, and much needed system and method for combating the harmful pathogens that are prevalent in several critical industries, such as the food products industry or the medical field. The present invention provides such a system and method by featuring an ozone sanitation device and system designed to sanitize various items or objects, such as food products or medical instruments.

It is another object of some embodiments of the present invention to provide an ozone sanitation device and system capable of inhibiting, controlling, and destroying harmful pathogens to allow food products to stay fresh longer and reduce the potential for the several harmful effects that can arise from contaminated food.

It is still another object of some embodiments of the present invention to provide an ozone sanitation device and system capable of restoring the water content (and water weight) to depleted or dehydrated food products, thus increasing their shelf life and vibrancy.

It is a further object of some embodiments of the present invention to provide an ozone sanitation device that may utilize pre-existing power and water resources, and any others that may be needed.

It is still a further object of some embodiments of the present invention to provide an ozone sanitation device and system that may be used at the site of the end market where the products are sold.

It is still a further object of some embodiments of the present invention to provide an ozone sanitation device that is easy to use, inexpensive, and extremely effective in combating harmful pathogens.

In accordance with the invention as embodied and broadly described herein, the present invention features an ozone sanitation device and system, as well as several methods of using the ozone sanitation device and system to sanitize, sterilize, and/or preserve various objects. The present invention is applicable to a number of industries, including particularly the food products industry and the medical field. However, for purposes of illustration, the disclosure set forth herein will focus on the exemplary embodiment of an ozone sanitation device and system designed to sanitize, sterilize, and preserve food products, as well as a method for sanitizing food product handlers, namely objects, devices, assemblies, and systems that are related to, come in contact with, or are otherwise associated with various food products.

The present invention further comprises a method for restoring much of the original water content and water weight to dehydrated foods through use of the ozone sanitation device and system, which not only functions to make the food products more attractive, but from a provider's standpoint, the food product would weigh more, thus items sold by weight would have a greater profit margin in contrast to an equal amount of raw product that was not treated with the present invention.

The present invention ozone sanitation device comprises a fully integrated ozone generation and wash machine designed for the use of food sterilization and preservation. The present invention further features a proprietary process for sanitizing food products that combines an ozone generator, capable of creating ozone gas, with a unique housing, as well as the unique ability to vary temperature and moisture for maximum efficacy in food sterilization and preservation. The ozone sanitation device is designed to be used on assorted food products, including fruits and vegetables (in whole or sliced form), seafood, poultry, and others, as well as various objects that come in contact with these food products, such as conveyors, display shelves, cutting boards, countertops, knives and other utensils or tools, and any others. The ozone sanitation device not only rids food products of harmful bacteria and viruses, but it also restores qualifying food products to (or nearly to) their original water weight, which in turn also reduces spoilage over time, thus creating a fresher, more healthy and less contaminated food product, as well as a longer and more vibrant shelf life and increasing the profit margin for grocers or food product providers. For example, grocers and others suffer greatly from the shrinkage of produce-type food products as a result of transport and display time, as most produce food products are sold by weight. The present invention functions to eliminate this and many other related problems.

The ozone sanitation device is preferably relatively small in size (e.g., about half the size of a home deep freezer) and easy to operate, with little installation requirements. In one preferred exemplary embodiment, installation is simple in that the only requirements for installation of the ozone sanitation device are hooking up the device to appropriate pre-existing plumbing and power or electricity resources, namely hot and cold water hookups, a drain hookup, and appliance quality electricity. These pre-existing resources make installation and use of the ozone sanitation device extremely simple.

Specifically, the present invention ozone sanitation device comprises an ozone sanitation system comprising a water supply supplying water to the system; an electrical power supply to supply power to the system; a temperature control module in connection with the water supply to control the temperature of the water; an ozone sanitation device removably coupled to the water and power supply, wherein the ozone sanitation device comprises at least one holding tank to house the water; a circulation system for circulating the water, wherein the circulation system comprises at least one pump, a venturi, and a series of lines extending between these; an ozone generator for producing and dispelling ozone, wherein the ozone generator injects ozone gas into the venturi where at least a portion of the water is mixed with the ozone gas to create a high concentrate ozonated water solution, the high concentrate ozonated water solution directed through the circulation system back to the holding tank; mixing means for mixing the high concentrate ozonated water solution with the water remaining in the holding tank to produce a treatment-ready ozonated water solution; means for applying the treatment-ready ozonated water solution to the object for treatment of the object; and a control module for controlling and operating the ozone sanitation device. The system further comprises one or more sanitation treatments corresponding to the treatment-ready ozonated water solution existing within the holding tank; and a re-circulation pump to recirculate and recycle the ozonated water in preparation of another treatment cycle.

In one exemplary embodiment, the system comprises a plurality of holding tanks comprising an ozone crisper tank, an ozone hydro-chiller tank, and a low-ozone concentrate tank.

In one exemplary embodiment, the ozone generator comprises a corona discharge-based ozone generator.

In one exemplary embodiment, the control module comprises a touch screen monitor with several selectable options or settings depending upon what action is desired and what food product is being treated. For example, a desired treatment of a food product may involve re-hydration or sterilization of the food product, or a desired treatment may involve the performance of both of these functions within the same treatment period. Also, the ozone sanitation device provides or allows for specific processes based on the item(s) or object(s) to be treated. Other types of control modules are contemplated.

The present invention further features several methods for sanitizing an object using the ozone sanitation device described herein.

Although the ozone sanitation device may be adaptable to provide numerous intended uses in relation to food products, perhaps its most beneficial use will be realized in an in-store setting or environment by grocers and other food providers seeking to improve the quality of their produce-type food products, as well as to reduce the time these products remain in their stores. As such, the present invention is preferably designed and manufactured for in-store use, wherein the device may be utilized by grocers prior to the displaying of their produce-type food products.

BRIEF DESCRIPTION OF THE DRAWINGS

In order that the manner in which the above-recited and other advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

It will be readily understood that the components of the present invention, as generally described and illustrated in the figures herein, could be arranged and designed in a wide variety of different configurations. Thus, the following more detailed description of the embodiments of the system and method of the present invention, as represented in FIGS. 1 through 5, is not intended to limit the scope of the invention, as claimed, but is merely representative of the presently preferred embodiments of the invention.

The presently preferred embodiments of the invention as set forth herein, will be best understood by reference to the drawings, wherein like parts are designated by like numerals throughout.

To better set forth the concepts and scope of the present invention, the following more detailed description is separated into two sections. The first section pertains to the specific elements, features, physical characteristics, function, intended uses, and various embodiments of the ozone sanitation device and system designed for the purpose of sanitizing an object or objects, namely food products or the systems, devices, and objects that come in contact with food products. The second section pertains to the several methods of sanitizing an object or objects to inhibit and prevent the existence and proliferation or growth of harmful pathogens. Each of the described methods utilizes one or more of the described embodiments of the ozone sanitation device and system as described and illustrated herein. However, other embodiments, methods, and intended uses, etc. are contemplated and are intended to be within the scope of the present invention as taught herein, wherein these other embodiments, methods, and intended uses will be recognized by or apparent and obvious to one ordinarily skilled in the art.

Ozone Sanitation Device and System

The present invention contemplates broad intended end uses for the ozone sanitation device, both in and out of the food products industry. For instance, the ozone sanitation device may be employed in restaurants, juice bars, meat and seafood counters, medical applications, and others for reducing salmonella in poultry, sanitizing fruit and vegetables before juicing, reducing pathogens, such as $E.\ coli$, in meat and seafood, and sanitizing water lines used in medical applications, respectively. Indeed, the many possible uses are too numerous to recite herein.

Although the ozone sanitation device and system of the present invention may be adapted or designed for use in a wide variety of environments and situations, the following detailed description focuses on an ozone sanitation device and system adapted for use within the food products industry. This particular focus is not meant to be limiting in any way, but is merely provided as one exemplary, preferred embodiment. Indeed, one ordinarily skilled in the art will recognize the several other uses and environments for which the ozone sanitation device and system may be adapted.

It is difficult for other sanitizing systems, such as chlorine systems, to compare to an ozone sanitation system. The ozone sanitation device and system of the present invention will allow supermarkets to market clean produce. This process is done at the sites of the individual stores, thus eliminating the chance for added contamination that often occurs in transportation and other processing procedures. Basically, the product is rinsed in cold water to retard the growth of the bacterium. It is then ozonated to reduce existing bacterium counts on the produce.

The ozone sanitation device and system is capable of performing many functions and performing them much more effectively than prior art systems. In addition, several benefits are realized using the present invention ozone sanitation device and system. Some of these functions and benefits include the ability to sanitize multiple harmful pathogens, the ability to eliminate yeast, molds, and spores, the ability to hydrocrisp many types of produce, the ability to extend the shelf life of food products, the device is adaptable for multiple uses other than fruits and vegetables (e.g., for ice, misting, bakery, seafood, poultry, and other meats, etc.), the ability to sanitize floor drains and sewer systems, the benefit of non-polluting the water and atmosphere from its use, the ability to reduce/eliminate odors, being safer for users of the device (e.g., employees) because the ozone is generated on-site so there are no other hazardous chemicals to purchase, store, or handle, the benefit of being user friendly and simple to operate, the ability to pay for itself by reducing the shrinkage potential of treated food products. Several other benefits, advantages, uses, etc. are also made possible as will be apparent to one of ordinary skill in the art, and as such are not recited herein.

The ozone sanitation device and system is also capable of incorporating other known sanitizing and disinfecting agents, such as chlorine, etc. When the ozone sanitation device is used with these other agents processing is safer because agents are metered for exact dilution, there is less employee handling of dangerous cleaning agents, the sanitation process is simpler and more precise, there exists machine timed cycles for accuracy and improved effectiveness, there exists the ability to hydrocrisp many types of produce, the shelf life of foods is extended, etc.

As stated, the preferred concept and function of the preferred embodiment of the present invention is to process and sanitize various food products, as well as to sanitize the objects, systems, or devices that come in contact with such food products using ozone. The particular processes or methods used, and the particular ozone systems utilized to carry out these methods, are diverse and encompass a broad variety of designs.

The present invention describes an ozone sanitation device and system designed to wash and sanitize an object or objects and to restore lost water content of dehydrated or partially dehydrated and shrunken food products. More particularly, the present invention describes an ozone sanitation device and system for use in a food product environment, wherein the device and system functions to lower the bacterial plate counts on these objects, inhibit and prevent the proliferation or growth of harmful pathogens, eliminate yeast, molds, and spores, hydrocrisp many types of produce, extend the shelf life of food products, eliminate or reduce odors, re-hydrate dehydrated vegetables and fruit, and others.

Figure 1:
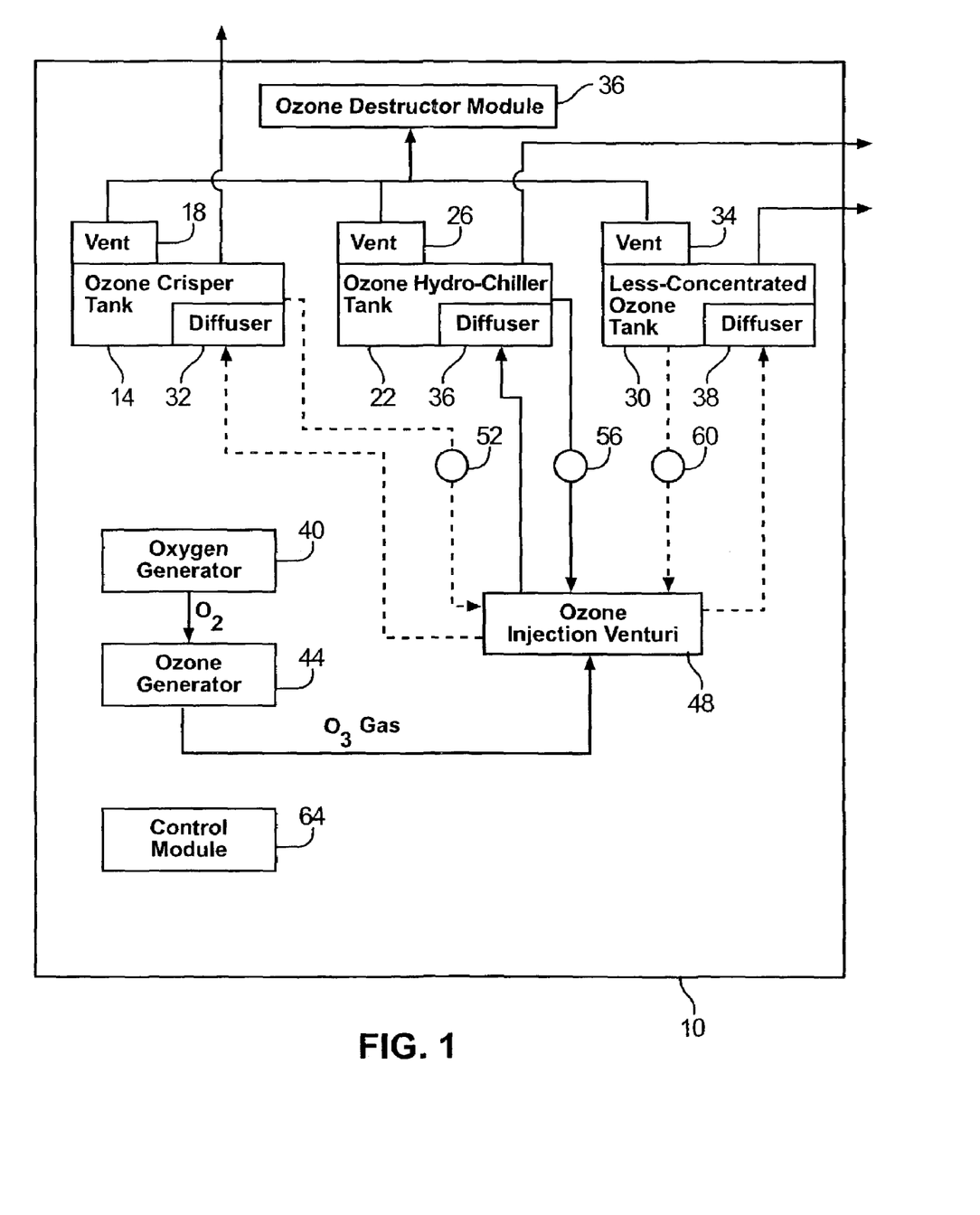
FIG. 1 illustrates a diagram of an ozone sanitation device according to one exemplary embodiment of the present invention.

With reference to FIG. 1, shown is ozone sanitation device 10 comprising a plurality circulation systems, namely an ozone crisper circulation system, an ozone hydro-chiller circulation system, and a respective low-ozone concentration circulation system. Each of these systems utilizes a holding tank, shown particularly as ozone crisper tank 14, ozone hydro-chiller tank 22, and low-ozone concentration tank 30, respectively. Each of holding tanks 14, 22, and 30 function to hold or house the filtered potable water received via an inlet feed (shown as inlet feed 8 in FIG. 2) from a water supply (either independent and external or internal to the device) and to store the ozone-water mixture during use of ozone sanitation device 10. Each of holding tanks 14, 22, and 30 comprise a diffuser 32, 36, and 38, respectively, for mixing the ozone that is injected into the respective holding tanks via ozone injection venturi 48, which receives the ozone from ozone generator 44. In addition, each of holding tanks 14, 22, and 30 comprise a vent means, shown as vents 18, 26, and 34 atop holding tanks 14, 22, and 30, respectively for venting any unused ozone. The vented ozone is not allowed to be released into the atmosphere or surrounding air due to its hazardous nature, therefore ozone sanitation device 10 further comprises an ozone destructor module 36 that causes any unused ozone released from either of vents 18, 26, and 34 to return to its natural resting state of equilibrium as oxygen ($O_2$) or water ($H_2O$).

Ozone sanitation device 10 further comprises an ozone generator 44 that functions to create, produce, or generate the ozone to be used in device 10. The preferred method of ozone production is via corona discharge, as explained below. In this process, oxygen is produced in oxygen generator 40. The oxygen produced in oxygen generator 40 is injected or delivered into ozone generator 44, where an additional oxygen atom is temporarily bonded to the oxygen molecule, thus resulting in $O_3$, or ozone. Stated differently, ozone generator 44 produces or creates a temporary triatomic oxygen substance ($O_3$) by adding an extra oxygen atom to the oxygen gas ($O_2$) produced from oxygen generator 40. The oxygen generator that delivers the oxygen to ozone generator 44 produces the high concentrations of ozone needed to sanitize a food product or object.

This temporary triatomic substance is commonly referred to as ozone and is an all natural cleaning agent. Ozone has a very short half-life compared to chemicals like chlorine. In addition, it has been proven that ozone is 52% stronger than the chemical chlorine in getting rid of approximately 90% of all the bacteria that is formed on food.

In short, ozone is a form of oxygen that acts differently in different situations, and is also highly unstable such that it almost immediately returns to its natural equilibrium or resting state of $O_2$ or $H_2O$ if allowed to do so. The present invention allows this transformation to occur, or rather induces this transformation, before returning it to the environment as high levels of ozone are hazardous. It should be noted that only recently has the Food and Drug Administration (FDA) approved ozone as a food additive/sterilizer.

There are two accepted and preferred methods employed to produce or generate ozone or ozone gas. The first method is via ultra-violet (UV) light, and the second is via corona discharge. The present invention ozone generator 44 may employ any method of producing ozone, including those not specifically recited herein, but preferably comprises producing ozone gas using the corona discharge method. The corona discharge method is the preferred method because it produces higher relative concentrations of ozone than the UV light method. Another benefit is that the ozone is generated by the present invention device system with the only input being electricity.

Once ozone is produced or generated, it is caused to exit ozone generator 44 where it is subsequently directed to and injected into ozone injection venturi 48. It should be noted that ozone sanitation device 10, and particularly each of the above-described holding tanks 14, 22, and 30 and their associate water circulation loops, may comprise separate independent venturies only to be used with a particular circulation loop, or ozone sanitation device 10 may utilize a universal venturi like ozone injection venturi 48 shown in FIGS. 1 and 2. Ozone injection venturi 48 receives water as stored within one or more of holding tanks 14, 22, and 30. Ozone injection venturi 48 also receives the ozone as generated or produced within ozone generator 44. As such, ozone injection venturi 48 functions to mix the ozone with the water to created ozonated water. Once mixed, the ozonated water is returned to a respective diffuser 32, 36, or 38 in holding tanks 14, 22, and 30, respectively. Diffusers 32, 36, and 38 function to mix the ozonated water with the remaining or residual water in the holding tank, thus allowing the holding tank to contain an identified quantity of ozonated water that can be extracted for treatment of one or more food products. Indeed, the concentration of ozone existing within any one of holding tanks 14, 22, and 30 at any given time following circulation may range between about 0.01 and 50 ppm. Preferably, ozone crisper tank 14 comprises a concentration of ozone between about 1 and 10 ppm, ozone hydro-chiller comprises an ozone concentration between about 1 and 5 ppm, and less-concentrated ozone tank 30 comprises an ozone concentration between about 0.01 and 2 ppm. Of course, these limits may be modified depending upon the intended use of device 10, as well as the type of food product or object being treated.

As shown in FIG. 1, the ozone hydro-chiller circulation process or system is active, such that any produced ozone is circulated into ozone hydro-chiller tank 22, and wherein any ozonated water used for treatment originates from tank 22. The process used to produce the ozonated water within hydro-chiller tank 22 comprises directing water from tank 22 to pump 56 and ultimately to ozone injection venturi 48 through the lines extending between tank 22 and ozone injection venturi 48. As mentioned, it is within venturi 48 that the potable water mixes with the ozone as produced and received from ozone generator 44. Ozone generator 44 also comprises a line extending therefrom to ozone injection venturi 48 to provide a means for delivering ozone to venturi 48. Once mixed, there is a return line extending from ozone injection venture 48 back to diffuser 36 located in ozone hydro-chiller tank 22, where the ozonated water is delivered and further mixed with the remaining potable water in tank 22 to create an identified quantity of ozonated water within tank 22, wherein the ozonated water comprises an identified concentration of ozone or ratio of ozone to potable water.

The other circulation processes or systems illustrated in FIG. 1, namely the ozone crisper and the low-ozone concentration systems, are shown as inactive as represented by the dotted lines. It should be emphasized that activation of only the hydro-chiller, as shown in FIG. 1, is merely exemplary as each of the systems, or any combination thereof, may be activated to treat a particular food product. Indeed, some food products will necessitate activation of both the hydro-chiller system and the ozone crisper system. As such, depending upon the circumstances, one or all of the available processes or systems may be utilized.

Once diffused into its respective holding tank, the ozonated water product stored in each of holding tanks 14, 22, and 30 is extracted out of these tanks and routed to one or more sanitizing chambers (shown in FIG. 2) where it used to treat the food products placed within the sanitizing chamber. This is explained in greater detail below in relation to the ozone sanitation system of the present invention.

Ozone sanitation device 10 also comprises a control module 64. Control module 64 is used to control all aspects of ozone sanitation device 10, and may comprise any type of control system or setup existing or commonly known in the art. In one exemplary embodiment, control module 64 comprises a graphical user interface in the form of a touch screen, various timers and device settings, etc. Displayed on the touch screen are several selectable items corresponding to a function, feature, attribute, setting, etc. of ozone sanitation device 10. Control module 64 comprises all of the necessary hardware and software components required to operate, maintain, and adapt ozone sanitation device 10. These are not specifically recited herein, but will be apparent to one of ordinary skill in the art. In essence, control module 64 comprises means for controlling ozone sanitation device 10 and comprises various selectable options or settings depending upon what action is desired and what food product is being treated. For example, a desired treatment of a food product may involve re-hydration or sterilization of the food product, or a desired treatment may involve the performance of both of these functions within the same treatment period. Also, ozone sanitation device 10 provides or allows for specific processes based on the item(s) or object(s) to be treated. Other types of control modules are contemplated.

Figure 2:
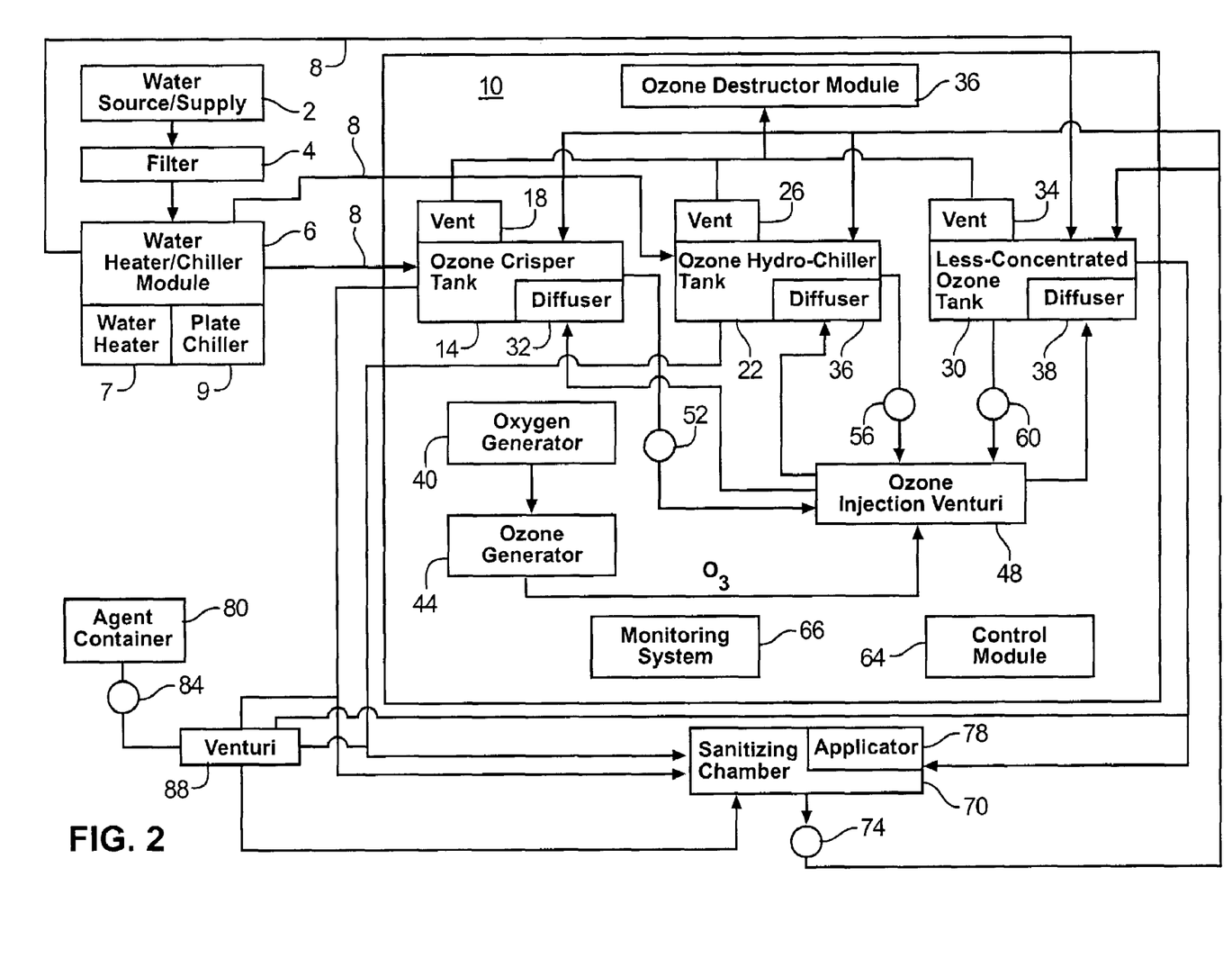
FIG. 2 illustrates a diagram of an ozone sanitation system according to one exemplary embodiment of the present invention.
Figure 3:
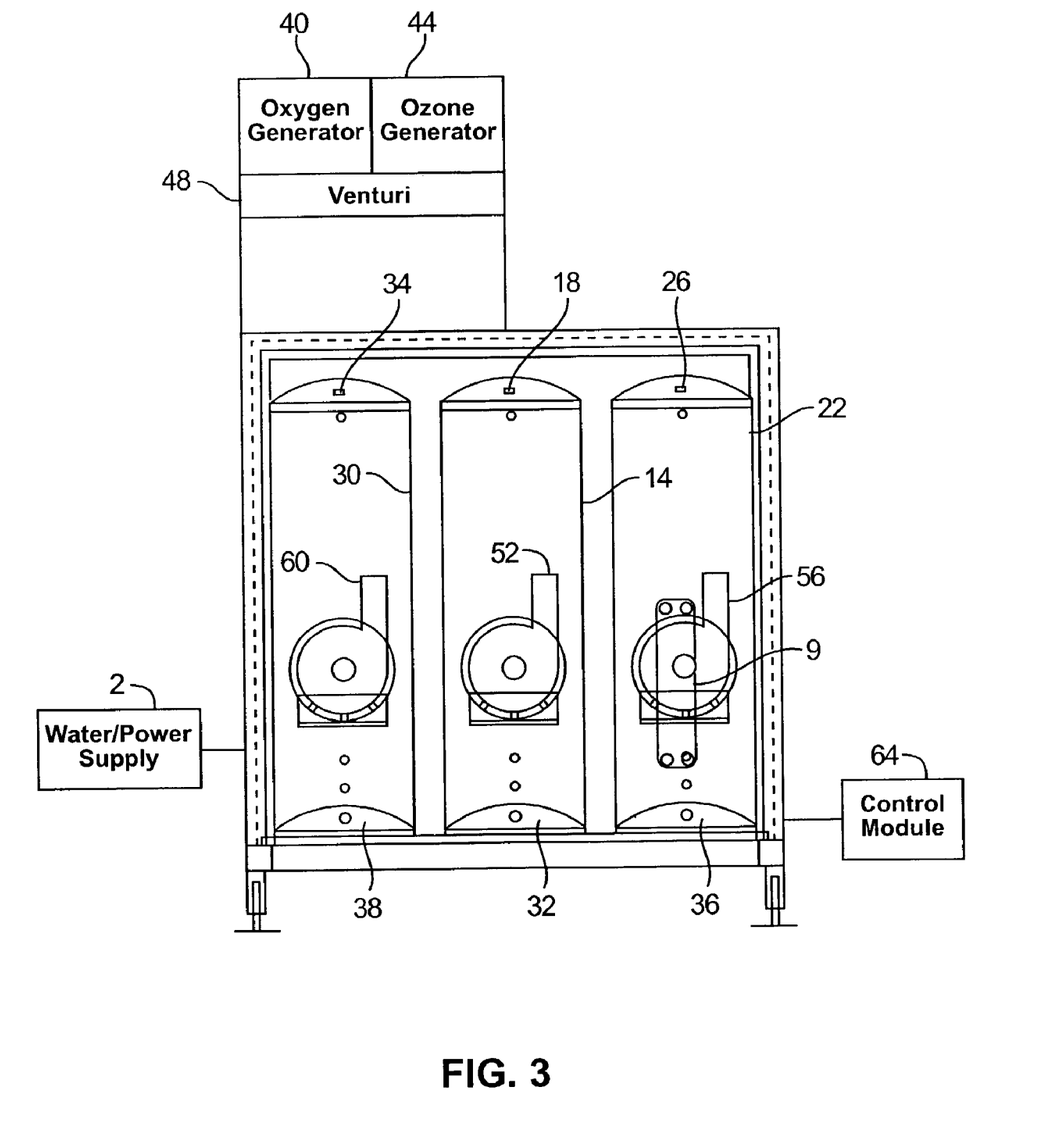
FIG. 3 illustrates a pictorial rendition of an ozone sanitation system according to one exemplary embodiment of the present invention.

FIGS. 2 and 3 illustrate one exemplary embodiment of an ozone sanitation system and method of sanitizing an object, wherein ozone sanitation device 10 is incorporated into an existing environment, namely a grocer's store, and utilizes pre-existing water, power, and drain resources. FIG. 2 illustrates the universal nature of the present invention as it is adaptable to many different types of environments, and has the ability to utilize many pre-existing resources, such as water and power hookups, drain systems, etc.

A unique ability of the present invention system is the ability to vary the temperature of the water and the moisture existing in the system. This is advantageous because a more calculated temperature serves to facilitate the washing and sanitation process rather than randomly or unknowingly selecting any temperature and/or moisture. The temperature and moisture settings are controlled and set by the user depending upon the treatment desired. As such, some treatments may call for a cold water ozone treatment, while others may require a hot water ozone treatment.

Specifically, in one exemplary embodiment of a cold water treatment, cold potable water is obtained from a water source or supply 2, and is preferably filtered using water filter 4. Upon being filtered, the water enters the water heater/chiller module 6 where it is chilled by some type of a refrigerant or coolant system, such as a plate chiller 9 having a freon compressor. Water flows through plate chiller 9 and is chilled to a temperature of between thirty-three and forty-five degrees Fahrenheit, and preferably between thirty-four and forty degrees Fahrenheit, by means of the refrigeration system existing within plate chiller 9. Once chilled, the water is then discharged into a holding tank, namely ozone hydro-chiller tank 22. From here, the water goes through a distribution or circulation loop where it is ozonated, recycled and re-used.

From hydro-chiller ozone tank 22, the water is then pumped by pump 56 into a line for distribution to sanitizing chamber 70. At the same time that the water is pumped through the distribution loop there is a portion of water slip streamed off the discharge of pump 56. This water is routed through an ozone injection venturi 48 for the injection of ozone from the ozone generator 44.

Similar to the cold water treatment, in another exemplary embodiment of a hot water treatment, hot potable water is discharged into the holding tank shown as ozone crisper tank 14. The hot water is then pumped from ozone crisper tank 14 by means of a pump 52. A lead distributes the water to sanitizing chamber 70. At the same time that the water is pumped through the distribution loop, there is a portion of water slip streamed off the discharge of pump 52, wherein the water is routed through ozone injection venturi 48 for the injection of ozone as generated from ozone generator 44.

Hydro-chilling is an important part of the conditioning process, while ozone crisping is designed to safely extend the shelf life of leafy vegetables. In addition, the quick cooling of the product also works to extend the life and safety of the treated product. These various cycles or treatments work together to make this concept and the present invention unique in the industry.

In regards to general ozone generation for all of the processed or circulation systems described herein, highly concentrated oxygen produced by oxygen generator 40 enters ozone generator 44 where ozone generator utilizes one or more methods of producing ozone (i.e., via UV light or corona discharge). The concentration levels of 0.01 to 50 ppm are then delivered to ozone injection venturi 48 for mixture with the water flow. Once mixed, this highly concentrated ozonated water is injected into one or any of diffusers 32, 36, and 38 existing within the bottom of holding tanks 14, 22, and 30. The existing pressure in the line makes the diffusers work more efficiently. Diffusers 32, 36, and 38 function to mix the ozonated water with the remaining water present in the holding tank to obtain an identified and desired ozone concentration. As stated, the desired ozone concentration preferably ranges between 0.01 and 50 ppm. Any excess gas that is generated inside holding tanks 14, 22, and 30 is vented to ozone destructor 36. Moreover, the water is continually circulated through the distribution loop from the holding tanks to the venturi and then to the diffuser as long as the device is turned on. This process ensures the ozone concentrations in the tank remain at a desired level.

The system shown in FIG. 2 further comprises a sanitizing chamber 70 in which an object, such as a food product, for washing and/or sanitizing may be placed for treatment. Sanitizing chamber 70 may comprise any type of proprietary or pre-existing container, basin, surface, etc. in which or whereon an object may be placed and ozonated water added and removed or drained. One such pre-existing container may be a sink as found in a grocer's store, wherein the sink comprises a plug assembly to stop the ozonated water, thus allowing it to pool, and a drain system for draining the ozonated and excess water therefrom when appropriate or desired. It should be noted that there are situations where a sanitation chamber may not be necessary, such as in the situation where a counter top or other large object is being treated.

Upon placing an object in sanitizing chamber 70 for treatment, ozonated water having a desired and identified concentration is routed through system lines to an applicator 78 that can be used to apply or supply the ozonated water to the object. Applicator 78 may be any known device, system, or assembly, such as a spray nozzle, an inlet feed (e.g., hose, pipe, etc.) directing the ozonated water into sanitation chamber 70, a misting device or assembly, or others. The particular type of applicator may or may not be important to the treatment process, however the present invention contemplates any known type of applicator.

The present invention system further comprises a re-circulation pump 74 designed to re-circulate the ozonated water through the distribution loop, and particularly back to the respective holding tank as shown in FIG. 2, thus allowing the ozonated water to be recycled and used over and over again. Re-circulation pump 74 may be coupled to sanitation chamber 70 to recycle the water drained therefrom. In the situation where a sanitation chamber is not used, other means may be employed to re-circulate and recycle the ozonated water so that it may be used again.

The system shown in FIG. 2 illustrates three separate and independent holding tanks, namely ozone crisper tank 14, ozone hydro-chilling tank 22, and low-ozone concentration tank 30. Each of these tanks is designed to hold or store therein water and ozonated water. As potable water is passed through water heater/chiller module 6, the water is then routed or delivered to these holding tanks as appropriately directed by the user of the system. Indeed, as mentioned above, any one or a combination of circulation systems for various treatments may be employed depending upon the intended use and the object being treated. Moreover, each holding tank preferably comprises insulation means in order to maintain the desired temperature of the water therein. The process that supplies ozone to ozone crisper tank 14 is exactly the same as the process used to supply ozone to ozone hydro-chill tank 22, except hot water is mixed in to achieve the proper temperature, such as to reconstitute green vegetables. The unused ozone gas is also vented the same on each of the three holding tanks.

The third holding tank is designed to supply ozonated water having lower ozone concentrations, typically ranging between about 0.05 and 1.5 ppm. Low-ozone concentration tank 30 and its associated treatment is designed for use in situations needing less of the ozone sanitation agent. Specifically, low-ozone concentration tank 30 comprises concentrations of agent that are lower than those found in ozone crisper tank 14 or ozone hydro-chiller tank 22. The ozonated water from low-ozone concentration tank 30 is specifically adapted for use in situations needing less concentration of sanitizing agent such as the bakery, water dispenser, or misting system of the store. Low-ozone concentration tank 30 is connected to a pump 60 designed to distribute the water through the distribution loop. Essentially, low-level ozone concentration treatment and the system providing such operates the same as the other treatments and associated equipment described above, except the venturi that injects the ozone into the circulated water is preferably smaller.

In one exemplary embodiment, an object to be treated or sanitized is placed in sanitizing chamber 70 consisting of a sink having a drain system. Control module 64 comprising a computerized touch screen is mounted above sanitizing chamber 70 and functions to control the cycles of treatment. A ball valve mounted under the sink controls the water flow out of the sink. The ball valve remains open during the rinsing process and closed during the sanitizing and disinfecting soaking processes. A re-circulation pump 74 is coupled to the drain system to recycle the water drained from the sink. Specifically, re-circulation pump 74 is designed to pump the water not used in the sink back to the respective holding tank where the water may be recharged with ozone.

The present invention further features the ability to treat objects with other agents, such as disinfectants or other cleaning agents, wherein these may be used within the system and in conjunction with the ozonated water. In one exemplary embodiment, a recyclable container 80 is placed in ozone sanitation device 10 and functions to house the disinfectant or cleaning agent. A metering/injector pump 84 is also utilized. The metering/injector pump draws the agents out of the container and injects them through the venturi into the water in the holding tank. A recyclable container is also placed under the sanitation chamber for receiving preservatives and/or shelf life extenders. A metering/injector pump 84 is mounted proximate sanitizing chamber 70 and draws the preservatives and/or shelf life extenders out of container 80 and injects them through a venturi 88 installed into the lines coming from the holding tanks leading to sanitizing chamber 70.

The present invention ozone sanitation system further comprises a monitoring system 66. Monitoring system 66 functions to control the concentration of agents or ozone existing within the system. As the agent or ozone flows through its respective circulation loop, it encounters a flow module comprising sensors. These sensors send the ozone concentration readings to a monitor, which in turn sends a signal to the PLC that controls the ozone generator or agent metering/injector pump, turning them on or off depending upon the concentration of agents or ozone in the water. Monitoring system 66 also comprises an air monitor mounted in the room where the sanitation chamber is located to monitor the ozone concentration in the surrounding air so that they do not reach harmful levels. The monitor will turn off ozone sanitation device 10 if the ozone levels become too high.

In regards to some of the benefits and advantages of the present invention, as a major benefit, any object washed by the ozone sanitation device can be preserved for a longer period of time because it reduces the bacteria growing on the object, which cause contamination and deterioration, as it cleans the object. The present invention ozone sanitation device can also provide a decrease in variable costs. Since the present invention can be utilized by end retailers the potential uses are immeasurable. In addition to that, the device and process of sanitizing is very universal, thus allowing them to be adaptable to a number of environments and situations. For example, as society is concerned with health issues, the amount of contaminants consumed with our fruits, meats, and vegetables is important. Consumers and producers want their foods to be as fresh and clean as possible. As a result the prior art devices discussed above have been developed for the purpose of treating food products. However, unlike these prior art devices, the present invention device and system will make it possible for fresh cut produce and meat to be fresher, preserved longer, and cleaned more naturally. For instance, when produce or meat is cut it collects a lot of bacteria onto the newly cut surfaces. However, after the food is cut it can be placed in the present invention ozone sanitation device and have nearly all existing bacteria killed. Also, unlike many prior art solution, the present invention has no side effects because it is a process that is more natural than irradiation or using chemicals, such as chlorine. Indeed, chlorine is a dangerous chemical that requires special handling and leaves residue on the product. Likewise, irradiation can only be performed on a limited amount of foods and is very expensive to perform. Also, irradiation can strip foods of Vitamin C by 5-10% and reduce Vitamin E levels to 25%. On the other hand, ozone is a natural sanitizer and its use has been shown to work remarkably well on are items such as fruit, vegetables, seafood, poultry, and other meats leaving these products in a more natural state.

Another benefit may be to organic food product providers. Organic food providers use manure to fertilize vegetables and organic crops. This makes the bacteria counts on foods grown close to the ground extremely high. Sanitizing with ozone can maintain the organic classification of the produce unlike other sanitizers.

Also ozone will reduce exterior pesticide residue on non-organic foods. The seafood and meat departments can wash any meat that can be rinsed with water. Ozone can reduce bacteria levels of many types of contaminants; some of which are very prominent on meat, such as $E.\ coli$ and salmonella.

The produce department could also implement the ozone into their existing misting systems, which would help reduce bacteria and infections, such as Legionnaires Disease, that can build up in their pipes.

Methods of Sanitizing an Object or Objects Using an Ozone Sanitation System

As the above discussion has focused on the particular elements and features of the present invention, the following sections focuses on the methods used to sanitize an object, as well as the several types of cycles and treatment methods made available through use of the ozone sanitation device described herein.

In its highest level of abstraction, the purpose and function of the present invention is to process and sanitize various objects, such as food products. The ozone sanitation device allows for great diversity in that it can be used to safely wash various foods, thus lowering bacterial plate counts existing on these foods. It can also be used to sanitize systems or objects that come in contact with food products, or it can be adapted to be used to sanitize larger objects, such as counter tops, pipes, floors, drains, etc. As such, the particular methods used for sanitizing an object are set forth below.

It is emphasized that in each of the methods below, no matter the particular treatment applied, varying of both temperature and moisture is contemplated. Although it may be desirable in some situations to not vary one or the other or both, varying of either or both in any of the methods identified below is made possible. Varying the temperature and moisture of the ozonated or agent-based water treatment provides a greater amount of control to the device and system, and allows more effective results to be obtained because various items requiring a higher temperature (or moisture) treatment to be effectively sanitized may be accommodated.

Figure 4:
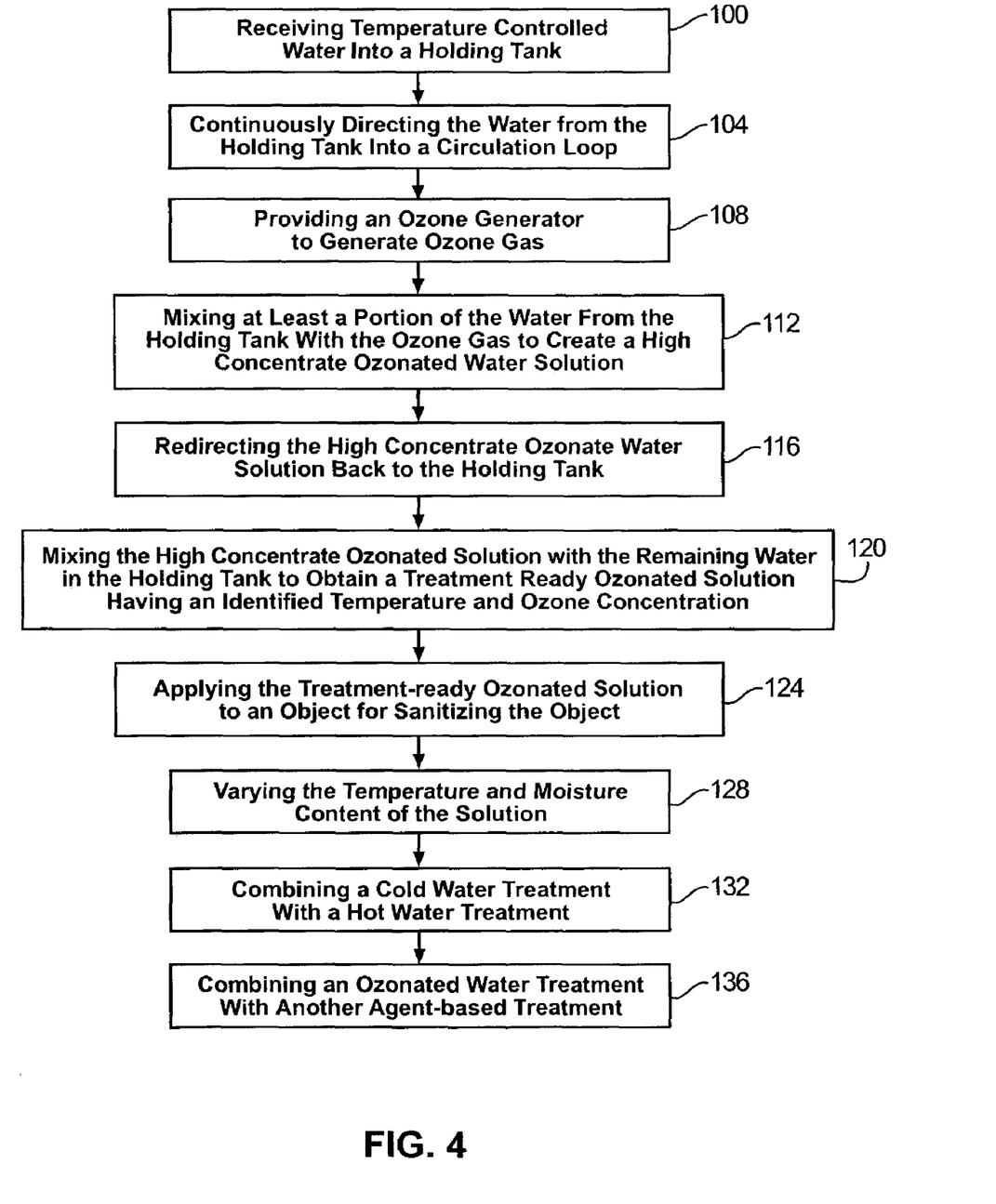
FIG. 4 illustrates a flow chart of a method for sanitizing an object.

Generally, the present invention features a method of sanitizing an object comprising the steps of: 100 receiving temperature and moisture content controlled water into a holding tank; 104 continuously directing the water from the holding tank into a circulation loop; 108 providing an ozone generator to generate ozone gas; 112 mixing at least a portion of the water being directed from the holding tank with the ozone gas to create a high concentrate ozonated water solution; 116 re-directing the high concentrate ozonated water solution to the holding tank; 120 mixing the high concentrate ozonated water solution with the water remaining in the holding tank to obtain a treatment-ready ozonated water solution having an identified ozone concentration; and 124 applying the treatment-ready ozonated water solution to an object to sanitize the object.

The method further comprises the step of 128 varying the temperature and moisture content of the ozonated water solution, either prior to or during treatment.

The method further comprises the step of 132 combining a cold water treatment with a hot water treatment.

The method further comprises the step of 136 combining an ozonated water treatment with another agent-based treatment. In one embodiment, the ozonated water is combined or mixed with another agent, such as a disinfectant or other cleaning agent, to obtain a mixed solution to be applied to the object. The mixed solution is then applied to the object for treatment. In another embodiment, the two treatments may be separate from one another and take place in different cycles.

Figure 5:
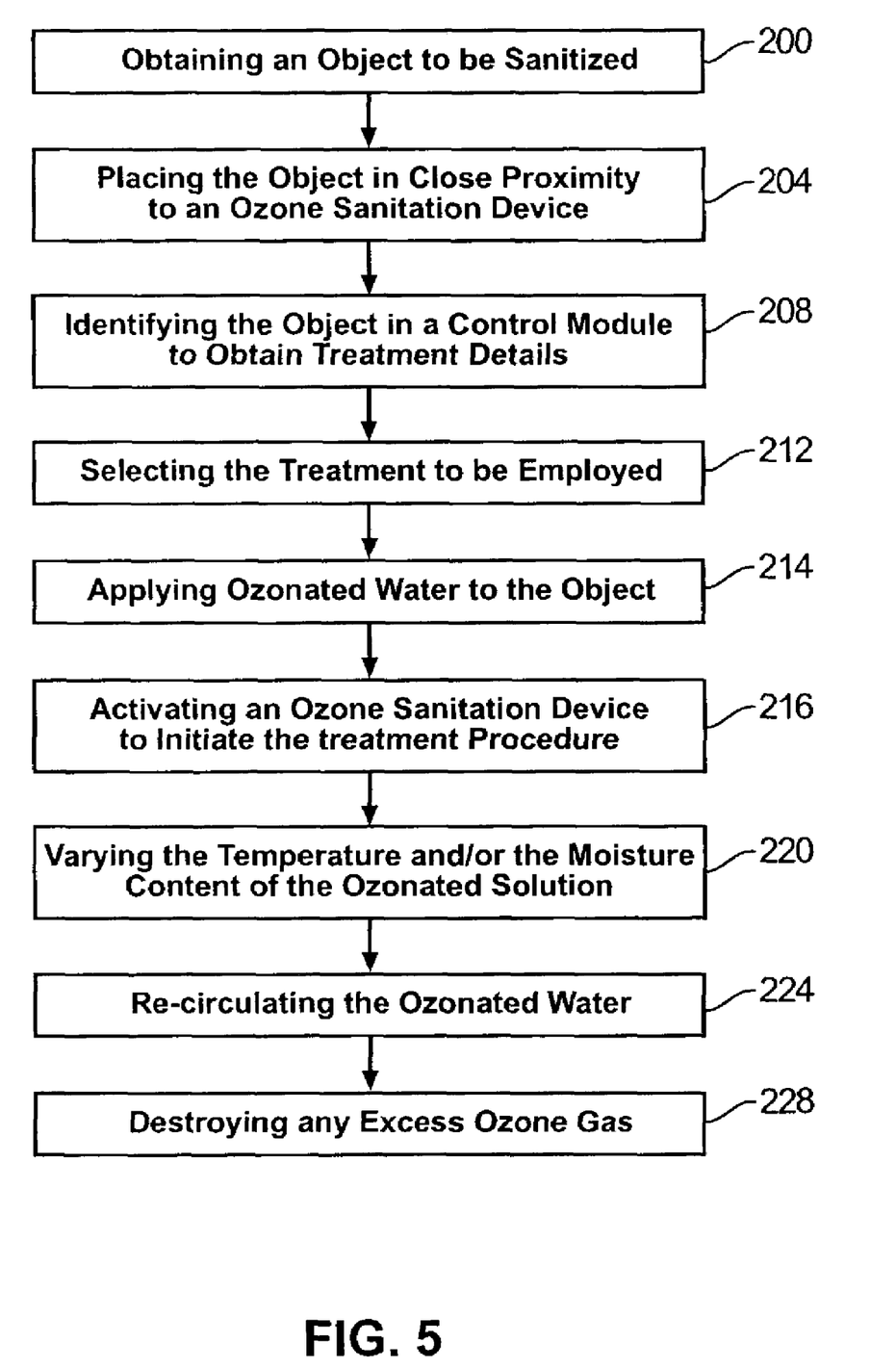
FIG. 5 illustrates a flow chart of a method for sanitizing an object.

More specifically, the present invention features a method of sanitizing an object using an ozone sanitation device. The method comprises the steps of: 200 obtaining an object to be sanitized, wherein the object may comprise a food product, a medical device or instrument, a surface, a pipe assembly, a drain system, or any other object that needs to be sanitized; 204 placing the object in proximity to an ozone sanitation device, wherein the ozone sanitation device comprises the elements and features discussed above; 208 identifying the object in the control module to obtain treatment details, such as concentration of ozone, which circulation treatment to employ, time of treatment, etc.; 212 selecting the treatment to be employed, wherein the treatment comprises applying ozonated water to the object, the ozonated water having an identified temperature and ozone concentration; 216 activating the ozone sanitation device to initiate the treatment procedure, thus exposing the object to the ozonated water; 220 varying the temperature and moisture content of the ozonated water as desired; 224 re-circulating the ozonated water; and 228 destroying any excess ozone gas. This method may be repeated as often as necessary.

In one exemplary embodiment, the intended use of the method involves washing, conditioning, crisping, and sanitizing leafy vegetables. The leaves of the vegetables are first trimmed. They are then placed in a container, such as a basket, that is then placed within the sanitation chamber. A spray wand is used to remove loose organics from the leaves. The drain in the sanitizing chamber remains open during the rinsing process. The next step is to select the food product on the touch screen of the control module (the control module is computerized and comprises a memory module that stores treatment cycles, times, etc. for various objects and is also programmable to include other objects). The greens cycle starts by filling the chamber with 80° to 112° ozonated water. The higher temperature is important to the opening of the product's cells. Opening cells allows them to absorb moisture and water, thus replacing that which was lost. The greens sit in the bath from three to ten minutes depending upon the time needed to reconstitute the product. The chamber then opens and drains. Once the chamber is drained the valve closes and the hydro-chill sanitizing treatment cycle starts. Chilled ozonated water is sprayed over the product by an overhead spray nozzle that covers the entire product bed. Once the chamber is full the water then shuts off. A sensor determines the tank is full and sends a signal to the input side of a PLC, which in turn sends an output signal to an electric solenoid valve and stops the flow of chilled ozonated water. This cycle holds the water in the chamber for three to ten minutes by a preset timer. The electric ball valve on the chamber is opened by an output signal from the PLC when the cycle is complete. The extra duty wash cycle extends the cleaning time by recycling the water before the chamber is emptied. The last cycle is a choice between cycles in which the chamber can be filled completely or just a spray is applied with the drain valve open or closed by a preset function in the PLC.

In another exemplary embodiment, the intended use of the method comprises washing, conditioning, crisping, and sanitizing whole vegetables. A container is used to hold prepared vegetables for processing. The container is placed into the chamber and processed for a preset time of three to seven minutes. The vegetables set in the ozonated water during this cycle. The settings for the ozone sanitation device are flexible and allow the operator to choose longer or extra cycles. An extra spray of chilled ozonated water may be added or the chamber can be filled or just rinsed with the electric ball valve opened by a preset function. The electric ball valve is opened when the treatment cycle is finished, wherein the container may then be removed.

In another exemplary embodiment, the intended use of the method comprises washing, conditioning, crisping, and sanitizing whole food products, such as whole melons. Treatment cycles for products such as whole melons start by placing the uncut melons into the sanitizing chamber. The melon surface is pre-rinsed with a spray wand. Visible dirt remaining on the melon surface must be removed with a bristle brush. Once the melons are cleaned the operator selects a preset cycle to fill the chamber with chilled ozonated water. They are processed for three to five minutes. The drain valve is then opened and the chamber is emptied. The basket can then be removed and the fruit placed on the shelf for sale.

In another exemplary embodiment, the intended use of the method comprises washing, conditioning, crisping, and sanitizing cut or sliced food products, such as cut fruit or vegetables. Cut fruit is processed by inserting the basket with the fruit into the sanitation chamber. The appropriate cycle is then selected, wherein the cut fruit sets in the ozonated water during this cycle. The device is designed to allow extra or extended cycles like an extra spray of chilled ozonated water with the electric ball valve or opened or closed by a preset function. The electric ball valve opens to drain the chamber.

Essentially, in reference to food products, the whole or precut food product is loaded into a treatment basket and then placed into the sanitizing chamber for treatment. Any excess dirt or remaining organic matter is removed and rinsed away. The cycle is then started using the control module. The product is pre-rinsed by a spray nozzle for the pre-set time, usually fifteen to thirty seconds, with the drain valve open. This removes the remaining organics and suspended solids. The drain valve then closes and, if the hydro-crisping cycle is being used, the vessel fills with warm potable water, approximately 99°, wherein this is sustained from five to thirty minutes. As mentioned, the moisture inside leafy vegetables starts to evaporate as soon as the vegetables are harvested. The present invention device and method of treatment causes the product cells to open and to absorb moisture, thus replacing lost water and adding firmness, which will ultimately increase the sale price of the vegetable.

Once the crisping cycle ends, the drain valve then opens. In most situations, the device is on a timer so that when the vessel is empty a rinse cycle starts. At this time, cold potable tap water is sprayed from the top of the vessel as well as from a rinse header in the bottom to flush any remaining dirt from the bottom of the vessel. Once the product is rinsed the drain valve closes. The spray nozzle now fills the vessel with chilled, ozonated water and/or other known sanitizing and disinfecting agents. The treated water is held in an ozone/chiller contact tank as discussed above. Preferably, the hydro-chilled holding tank is engineered to hold just enough water for one cycle. The treated water is continuously recycled and passes through a venturi by means of a recycle pump. When ozone is used the residual gas is passed from the top of the closed holding tank into an ozone destructor to eliminate excess ozone gas in the room. The food product sits in the treated water for the preset time, usually three to fifteen minutes, with five being optimum. Upon completion of the preset treatment time, the bacteria levels are reduced and the product is chilled. The outcome is a fresher, safer, chilled product with a longer shelf life. At this time, the drain valve opens and after the preset time, in which the vessel empties, a final rinse starts. The product is rinsed with treated, chilled water for the preset time, preferably thirty seconds. After a short drain period the cycle is now complete and the product can now be unloaded. The process is repeatable any number of times.

The present invention further features a method of sanitizing a food product handler. This particular method is similar to that discussed above only it pertains to a food product handler that may be defined as any object, device, system, or mechanism associated with the preparation, processing, packaging, transporting, displaying, or otherwise handling of various food products, as well as anything that comes in contact with a food product on a regular basis.

The following example illustrates and present the effects of the ozone sanitation system on harmful pathogens, namely the preventative and inhibition effects of the ozone sanitation system and methods against bacteria, viruses, and spoilage. This example is not intended to be limiting in any way, but is merely illustrative of the benefits and advantages of utilizing an ozone sanitation system to sanitize various objects or food products.

EXAMPLE ONE

The present example illustrates a sanitation procedure. In this example, ozone sanitation treatments are used to show their effectiveness on various food products, as well as to illustrate the benefits of ozone sanitation treatments over traditional sanitation treatments, such as chlorine treatments. To illustrate, comparisons of aerobic plate counts and yeast molds existing before and after treatment are made to determine the effectiveness of ozone sanitation over traditional sanitation procedures.

The study involves taking several food products, such as oranges, lettuce, melons, corn, and other produce items and subjecting them to an ozone sanitation process as described and shown herein. A high success rate exists where the total bacteria and yeast mold pathogens are reduced 99% upon initial sanitation, and 90% or higher after twenty-four hours of the sanitation process.

The study involves taking cultures form the surface of these food products and letting them grow for a period of two weeks. At the conclusion of the two weeks, these cultures are taken and a portion of them are treated using an ozonated water solution and a portion are treated using traditional chlorine sanitation procedures. Those cultures treated with ozone are markedly cleaner and show a much more significant in total reduction of pathogens. Indeed, the ozone is capable of wiping out many of the harmful pathogens that exist within the cultures.

In another test, one half of a quantity of Romaine lettuce is sanitized with an ozonated water solution. The other half is washed using traditional washing methods. The produce is then stored for two weeks. At the end of the two week period, the two are compared, with the ozone treated lettuce produce containing significantly less pathogens than the non-ozone treated lettuce.

From these tests, it is impossible to determine how much the ozone sanitation device and process could save supermarkets in waste reduction. In addition to the lengthened shelf-life resulting from ozone sanitation, the present invention features a re-hydration cycle that restores wilted produce to its natural garden freshness.

Still further, when produce is cut for packaging the knife can spread pathogens from the outside of the product to the surface the knife touches. However, the effects of pathogens on cut fruit can be significantly reduced through use of the ozone sanitation device and one or more methods of sanitizing the cut fruit. Because of its natural composition, basically any food product that can be washed with water can be sanitized with the ozone sanitation device.

Finally, finger foods such as grapes and strawberries are treated just before they are placed on store shelves using the in-store ozone sanitation device of the present invention. This helps make them safe for customers to snack on while they travel home. Essentially, the ozone sanitation device is superior to the traditional processing procedures that many supermarkets use on a daily basis. Thus, if used properly, it has the ability to dramatically reduce bacteria and yeast molds and prevent any potential internalization of microorganisms in the produce compared to existing procedures.

The present invention may be embodied in other specific forms without departing from its spirit or essential characteristics. Moreover, the described embodiments are to be considered, in all respects, only illustrative and not restrictive. As such, the scope of the invention is indicated by the appended claims, rather than by the foregoing description. All changes that come within the meaning and range of equivalency of the claims are to be embraced within their scope.

What is claimed and desired to be secured by Letters Patent is:

1. A method of reducing pathogens associated with an object, wherein said object is one of (i) a fruit and (ii) a vegetable the method comprising:
   receiving temperature controlled water into a holding tank;
   continuously directing said water from said holding tank into a circulation loop;
   providing an ozone generator to generate ozone gas;
   mixing at least a portion of said water from said holding tank with said ozone gas to create a high concentrate ozonated water solution;
   re-directing said high concentrate ozonated water solution back to said holding tank;
   mixing said high concentrate ozonated water solution with said water remaining in said holding tank to obtain a treatment-ready ozonated water solution having an identified temperature and ozone concentration;
   varying a temperature and moisture content of said ozonated water solution, wherein the temperature of said ozonated water solution is between about 80 degrees Fahrenheit and about 112 degrees Fahrenheit;
   applying said treatment-ready ozonated water solution to said object to reduce pathogens associated with said object; and
   restoring a water content amount to said object through application of said ozonated water solution onto said object at said temperature.

2. The method of claim 1, wherein said varying said temperature and moisture content of said ozonated water solution is performed prior to said application.

3. The method of claim 2, further comprising varying said temperature of said ozonated water solution to between about 33 degrees Fahrenheit and about 45 degrees Fahrenheit and applying said ozonated water solution to said object to chill said object and increase retention of said water content after the step of applying said ozonated water having a temperature between about 80 degrees Fahrenheit and about 112 degrees Fahrenheit.

4. The method of claim 1, further comprising combining said ozonated water solution with another agent-based solution prior to said application on said object.

5. The method of claim 4, wherein said another agent-based solution is at least one of (i) a disinfectant and (ii) a cleaning agent.

6. The method of claim 2, further comprising applying an agent-based solution to said object, wherein said agent-based solution and said ozonated water solution are alternatively applied.

7. The method of claim 6, wherein said another agent-based solution is at least one of (i) a disinfectant and (ii) a cleaning agent.

8. The method of claim 1, wherein said varying said temperature and said moisture content of said ozonated water solution is performed during application of said ozonated water solution onto said object.

9. The method of claim 1, wherein said high concentrate ozonated water solution has an ozone concentration in the range selected from one of the following:
   (i) between about 0.01 ppm and about 50 ppm; and
   (ii) between about 1 ppm and about 10 ppm.

10. A method for reducing pathogens associated with a food item, wherein said food item is one of (i) a fruit and (ii) a vegetable the method comprising:
    using an ozone generator to generate ozone gas;
    mixing said ozone gas with water to create a high concentrated, ozonated water solution, wherein the temperature of said ozonated water solution is between about 80 degrees Fahrenheit and about 112 degrees Fahrenheit;
    reducing pathogens associated with said food item upon application of said ozonated water solution onto said food item at said temperature; and
    restoring a water content amount to cells of said food item upon application of said ozonated water solution onto said food item at said temperature.

11. The method of claim 10, further comprising applying an agent-based solution to said food item, wherein said agent-based solution and said ozonated water solution are alternatively applied, wherein said another agent-based solution is at least one of (i) a disinfectant and (ii) a cleaning agent.

12. The method of claim 11, further comprising combining a cold water treatment with a hot water treatment.

13. The method of claim 10, further comprising combining said ozonated water solution with another agent-based solution prior to said application onto said food item, wherein said another agent-based solution is at least one of (i) a disinfectant and (ii) a cleaning agent.

14. The method of claim 13, further comprising varying said temperature of said ozonated water solution to between about 33 degrees Fahrenheit and about 45 degrees Fahrenheit and applying said ozonated water solution to said object to chill said object and increase retention of said water content after the step of applying said ozonated water having a temperature between about 80 degrees Fahrenheit and about 112 degrees Fahrenheit.

15. The method of claim 10, wherein said high concentrated, ozonated water solution has an ozone concentration in the range selected from one of the following:

(i) between about 0.01 ppm and about 50 ppm; and (ii) between about 1 ppm and about 10 ppm.

16. A method for reducing pathogens associated with a food item, wherein said food item is one of (i) a fruit and (ii) a vegetable the method comprising:

using an ozone generator to generate ozone gas;

mixing said ozone gas with water to create a high concentrated, ozonated water solution, wherein the temperature of said ozonated water solution is between about 80 degrees Fahrenheit and about 112 degrees Fahrenheit;

reducing pathogens associated with said food item upon application of said ozonated water solution onto said food item at said temperature;

restoring a water content amount to cells of said food item by opening said cells though application of said ozonated water solution onto said food item at said temperature; and closing said cells to increase retention of said water content though varying said temperature of said ozonated water solution to between about 33 degrees Fahrenheit and about 45 degrees Fahrenheit and applying said ozonated water solution to said food item.

17. The method of claim 16, wherein said high concentrated, ozonated water solution has an ozone concentration in the range selected from one of the following:

(i) between about 0.01 ppm and about 50 ppm; and (ii) between about 1 ppm and about 10 ppm.

18. The method of claim 16, further comprising combining said ozonated water solution with another agent-based solution prior to said application onto said food item, wherein said another agent-based solution is at least one of (i) a disinfectant and (ii) a cleaning agent.

19. The method of claim 16, further comprising applying an agent-based solution to said food item, wherein said agent-based solution and said ozonated water solution are alternatively applied, wherein said another agent-based solution is at least one of (i) a disinfectant and (ii) a cleaning agent.

* * * * *